United States Patent [19]

Locko et al.

[11] Patent Number: 4,663,488

[45] Date of Patent: May 5, 1987

[54] OPPENAUER OXIDATION OF GERANIOL/NEROL

[75] Inventors: George A. Locko, Trenton, N.J.; Walter C. Frank, Holland, Pa.

[73] Assignee: Union Camp Corporation, Wayne, N.J.

[21] Appl. No.: 835,203

[22] Filed: Mar. 3, 1986

[51] Int. Cl.$^4$ .............................................. C07C 45/27
[52] U.S. Cl. .................................................... 568/485
[58] Field of Search ........................................ 568/485

[56] References Cited

U.S. PATENT DOCUMENTS 4,055,601 10/1977 Ehmann .............................. 568/390

FOREIGN PATENT DOCUMENTS 624222 7/1961 Canada ................................. 568/485
1381587 12/1974 United Kingdom ................ 568/485

OTHER PUBLICATIONS

Djerassi, "Organic Reactions", vol. VI, Chapter 5, pp. 208–269, John Wiley & Sons, London.
Adkins et al., "Amer. Chem. Soc." vol. 71 (1949), pp. 3622–3629.

*Primary Examiner*—Werren B. Lone
*Attorney, Agent, or Firm*—Kane, Dalsimer, Kane, Sullivan and Kurucz

[57] ABSTRACT

The disclosure is of an improved process for the Oppenauer oxidation of geraniol/nerol to obtain citral. The improvement comprises the use of selected tertiary aldehydes as hydrogen acceptors.

6 Claims, No Drawings

OPPENAUER OXIDATION OF GERANIOL/NEROL

BACKGROUND OF THE INVENTION

1. Field of the Invention

The invention relates to an improved method of preparing citral from geraniol/nerol under selected Oppenauer oxidation conditions.

2. Brief Description of the Prior Art

Citral (3,7-dimethyl-2,6-octadienal) is a valuable and widely-used ingredient of lemon flavor and fragrance compositions. It is also useful as an intermediate in the preparation of the ionone family of aroma chemicals and in the production of vitamin A.

It is usually made by the oxidation of geraniol, nerol or mixtures of geraniol or nerol. One widely-practiced oxidation process is vapor-phase air-oxidation which is carried out at a high temperature in the presence of a catalytic metal, see for example British Pat. No. 1,381,587. The harsh conditions of this process lead to the formation of numerous by-products which contribute to lowering the yield and aroma quality of the prime product.

In contrast, the Oppenauer oxidation process, a well-known chemical technique for converting alcohols to ketones or aldehydes (see "Organic Reactions," Vol VI, Chapter 5, John Wiley and Sons, Inc.), has potential for giving citral of excellent aroma quality and in high chemical yield because it is carried out under mild conditions—at low temperatures and in the liquid phase. Oppenauer oxidation in general involves the transfer of two hydrogen atoms to a hydrogen acceptor compound, usually a ketone or aldehyde. Although the mechanism of the transfer is a matter of speculation, it is catalyzed by the presence of aluminum aryloxides or aluminum alkoxides. Although a wide variety of aluminum alkoxides and aryloxides may be added to the Oppenauer oxidation reaction mixture to initiate catalysis, it has been suggested by Djerassi (Organic Reactions, supra., page 209) and others that the true catalyst in the oxidation is an aluminum alkoxide or aryloxide generated in-situ from the alcohol reactant itself upon undergoing an exchange reaction with the additive aluminum alkoxide/aryloxide.

In any event, the Oppenauer oxidation reaction is complex. There are occurring simultaneously a number of reverse and side reactions. The role of the catalyst structure in regard to the main and side reactions is not fully understood. One side reaction which is particularly troublesome in the oxidation of an allylic alcohol to the corresponding aldehyde, particularly when employing an aliphatic aldehyde as the hydrogen acceptor, is the so-called "crossed-Tishchenko" reaction between the hydrogen acceptor and the alcohol starting material to obtain the corresponding ester. In the oxidation of geraniol/nerol to citral, the by-product is the mixture of geranyl/neryl esters which may be difficult to separate from the desired geranial/neral. Another troublesome side reaction is the "simple Tischenko" reaction involving an ester formed by the reaction of two moles of the aliphatic hydrogen acceptor. This side reaction reduces the concentration of hydrogen acceptor and thereby lowers the conversion of the alcohol to the desired aldehyde product.

U.S. Pat. No. 4,055,601 describes the use of furfural as the hydrogen acceptor for the conversion of 3-substituted and 3,3-disubstituted allyl alcohols, including geraniol, to their corresponding aldehydes. Although this process offers a considerable improvement over the methodology of the prior art because furfural does not undergo an aldol condensation with the aldehyde product, leading to a reduction in the amount of aluminum catalyst used to catalytic quantities, there are still many important disadvantages that remain when it is applied to making aroma-quality citral. For example, to make a purified form of citral economically, one needs to distill the crude reaction mixture, thereby removing the large excess of unreacted hydrogen acceptor and co-product alcohol. Furfuryl alcohol boils at a temperature of 170° C. and furfural at 162° C. These two compounds are therefore difficult to separate from each other by distillation. Also, since they are relatively high boiling compounds, their distillation will result in some loss of citral (boiling point 229° C.) which is heat-sensitive. Further, the use of furfural as a hydrogen acceptor is not advantageous in that it oxidizes readily in air and decomposes in the presence of a base, which complicates storage and handling. Furfuryl alcohol decomposes in acid media.

Thus, the process of the U.S. Pat. No. 4,055,601 is only advantageous if the furfural is used under conditions such that it is all consumed and the crude citral converted to pseudo-ionone. There is then a considerable amount of geraniol/nerol which remains unconverted and must be recovered separately from the furfuryl alcohol for return to the start of process.

Tertiary aldehydes, like furfural and benzaldehyde, have no alpha-hydrogens. If they acted as Oppenauer acceptors, they should not give Aldol condensation by-products. However, they are highly sterically hindered and there are no literature reports of the use of such a tertiary aldehyde as an Oppenauer oxidant in the preparation of another ketone or aldehyde, in spite of the report of Adkins, et al. (J. Amer. Chem. Soc., Vol. 71, p. 3622) that the oxidation potential of trimethylacetaldehyde is only a little less than furfural.

By the method of the present invention, pure citral of excellent aroma and flavor quality may be prepared in improved yields, in the presence of a particular kind of hydrogen acceptor and under Oppenauer conditions, with reduced amounts of the undesired by-product Tishchenko esters and almost complete conversion of the feed geraniol/nerol. The tertiary aldehydes employed are much more stable in air, bases, and acids than either furfural or its corresponding alcohol. Unreacted tertiary aldehydes employed herein and their co-alcohols have relatively low boiling points, which are at least twenty degrees apart, thus leading to superior recovery of pure citral by-product alcohol, and of any unreacted tertiary aldehyde by simple distillation. The recovered tertiary alcohol may be separately oxidized back to the aldehyde and the aldehyde reused in future preparations.

SUMMARY OF THE INVENTION

The invention comprises in the Oppenauer oxidation of geraniol/nerol to prepare citral in the presence of an Oppenauer oxidation catalyst and a hydrogen acceptor, the improvement which comprises; carrying out said oxidation in the presence of a tertiary aldehyde as said hydrogen acceptor.

DETAILED DESCRIPTION OF THE PREFERRED EMBODIMENTS OF THE INVENTION

It has been proposed that the mechanism of the oxidation of geraniol/nerol to obtain citral under Oppenauer conditions proceeds according to the schematic formula:

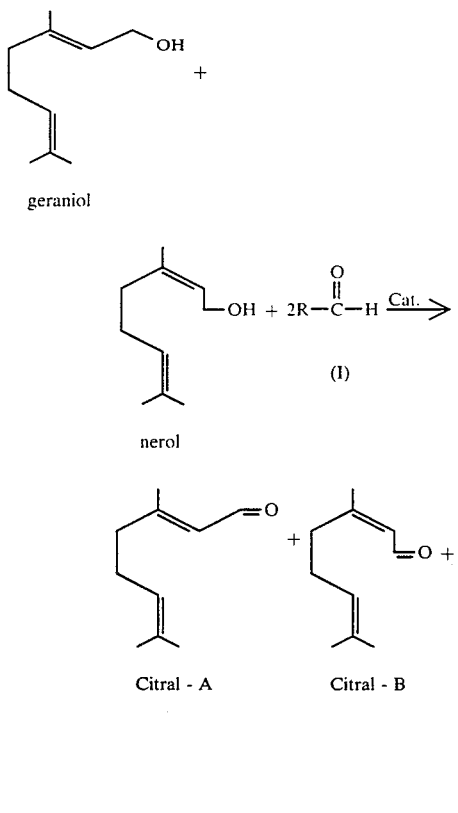

The method of the invention is based on the discovery that tertiary aldehydes despite the steric hindrance of the aldehyde group are excellent hydrogen acceptors, i.e., oxidizing agents in the Oppenauer conversion of geraniol/nerol to citral. Thus, in the above schematic formula (I);

represents a tertiary aldehyde hydrogen acceptor (R being a hydrocarbyl moiety) and the catalyst is an aluminum alkoxide or an aluminum aryloxide.

Representative tertiary aldehydes employed in the improved method of the invention are selected from those of the formula:

wherein $R_1$, $R_2$ and $R_3$ are each independently selected from alkyl, and alkenyl, and $R_1$ and $R_2$ taken together with the carbon atom to which they are attached represent cycloalkyl of 5 to 6 carbon atoms, inclusive, or cycloalkenyl of 5 to 6 carbon atoms, inclusive. Preferably, the tertiary aldehyde (II) selected will be one which is stable in air, acid, and base media.

The term "hydrocarbyl" as used herein means the monovalent moiety obtained upon removal of a hydrogen atom from a parent hydrocarbon. Representative of hydrocarbyl are alkyl of 1 to 5 carbon atoms, inclusive, such as methyl, ethyl, propyl, butyl, pentyl, alkenyl of 2 to 5 carbon atoms, inclusive, as vinyl, allyl, butenyl, pentenyl, and isomeric forms thereof.

Representative of tertiary aldehydes of the formula (II) given above, preferably employed in the method of the invention are trimethylacetaldehyde (2,2-dimethyl propanal), 2,2-dimethylbutanal, 2-methyl-2-ethyl butanal, 2,2-dimethylpent-4-enal (DIMPAL); 1-methyl-3 cyclohexene-1-carboxaldehyde, 1-methyl-cyclopentane-1-carboxaldehyde; and the like.

The improved method of the invention may be carried out under a wide variety of conditions. In the improved method of the present invention, selected Oppenauer reaction conditions are preferred.

Aluminum alkoxides and aluminum aryloxides which are used in the method of the invention as Oppenauer catalysts or to generate the catalyst in-situ are well-known compounds and are represented by aluminum isopropoxide, aluminum t-butoxide, aluminum phenoxide and the like.

In the method of the invention, the catalyst is employed in a catalytic proportion. In general, a catalytic proportion may be obtained by the addition of from about 0.1 to 15 mol percent (based on the weight of geraniol/nerol to the reaction mixture. Preferably about 1 to 5 mol percent is used.

The proportion of geraniol/nerol employed in regard to the proportion of hydrogen acceptor is not critical except insofar as it is advantageous to employ a molar excess of the hydrogen acceptor. In general, a molar ratio of geraniol/nerol to hydrogen acceptor will be within the range of from about 1:0.9 to about 1:10; preferably 1:1 to 1:1.5.

The Oppenauer oxidation of an alcohol is an exothermic reaction and the reaction-mixture need not be heated to initiate the reaction. Preferably the reaction is controlled so that the reaction mixture temperature does not exceed about 70° C. Control may be achieved by any conventional technique such as by controlling the rate of addition of reactants and/or hydrogen acceptor. A relatively low temperature (preferably 10° C. to 60° C.) is very important, for the product citral is heat-sensitive, undergoing aldol self-condensation at higher temperatures. Under the temperature conditions employed in the improved method of the invention, the side reactions resulting in undesirable compounds, such as isocitrals and dimers are minimized.

The method of the invention may be carried out under sub-atmospheric, super-atmospheric or atmospheric pressures.

Progress of the reaction towards formation of the desired aldehyde product may be followed by conventional analytical techniques. Upon completion of the reaction and removal of the catalyst the desired product may be separated from the reaction mixture by conventional fractional vacuum distillation.

A most important advantage of the present invention is the relatively low boiling points of the tertiary aldehydes selected. For example, the boiling point of trimethylacetaldehyde is 78° C., that of DIMPAL is 125° C. These are considerably lower than that of citral. Since citral is heat sensitive, the lower the temperature at which the unreacted aldehyde and its co-product or derivative alcohol can be removed by distillation, the higher will be the yield of pure citral.

Another important advantage of the improved method of the invention is the ease of separation that can be achieved between the unreacted tertiary aldehyde and its co-product derivative alcohol. Again, the trimethylacetaldehyde and DIMPAL are preferred because of the considerable difference in the boiling points of these compounds and their derivative alcohols, [trimethylacetaldehyde-neopentyl alcohol (78° C. and 114° C.) DIMPAL-DIMPOL (125° C. and 153° C.)]. These compare most favorably against furfural-furfuryl alcohol (162° C. and 170° C.), the hydrogen acceptor and its co-product of the prior art, where, in contrast, much less of either the desired product citral or of the hydrogen acceptor can be recovered for future reuse. Moreover, the tertiary aldehydes exhibit stability in the presence of air, acids, and bases.

The following examples describe the manner and process of making and using the invention and sets forth the best mode contemplated by the inventor of carrying out the invention but are not to be construed as limiting.

EXAMPLE 1

This examples illustrates the oxidation of geraniol to citral using trimethylacetaldehyde as a hydrogen acceptor. A flask was charged with 25 g of distilled geraniol and 0.62 g aluminum isopropoxide (2.5 wt % based on geraniol) and was stirred for one hour. 21.1 g trimethylacetaldehyde was added at ambient temperature over 10 minutes and the reaction was stirred an additional five hours. Internal standard gas-liquid gas chromotographic analysis of the crude reaction mixture then showed a 92.3% molar yield of citral.

EXAMPLE 2

This example illustrates the oxidation of geraniol to citral using DIMPAL as a hydrogen acceptor. A flask was charged with 25 g of distilled geraniol and 0.61 g aluminum isopropoxide (2.5 wt. % based on geraniol) and was stirred for three hours at ambient temperature. 28 g DIMPAL was added over 10 minutes and stirred an additional 1.5 hours. Internal standard g.c. analysis of the crude reaction mixture then showed a 97.5% molar yield of citral.

EXAMPLE 3

This example illustrates the oxidation of geraniol/-nerol to citral using DIMPAL as a hydrogen acceptor. A flask was charged with 401 grams of a mixture of geraniol and nerol (in a 2.5:1.0 ratio) and 10.5 g of aluminum isopropoxide (2.6% by weight based on geraniol/nerol). 366 g of DIMPAL was added over 20 minutes and the reaction was stirred for an additional two hours at approximately 40° C. Analysis of the crude reaction mixtue by Internal standard gas-liquid phase chromotography showed a 92% molar yield of citral.

The crude reaction mixture was washed with dilute acid, dried, and distilled through a glass-bead-packed column at reduced pressure to give a 330 g distillation cut containing 290 g of the by-product alcohol derived frim DIMPAL, and 39 g of recovered DIMPAL. The distillation residue, 394 g, consisted of citral (361 g) and nerol/geraniol (23 g), giving a distillation accountability of 99% on citrals.

What is claimed:

1. In a process for producing citral from geraniol/-nerol using an Oppenauer oxidation in the presence of an Oppenauer oxidation catalyst and a hydrogen acceptor, the improvement which comprises carrying out said oxidation in the presence of a tertiary aldehyde as said hydrogen acceptor and recovering the citral by distillation of the hydrogen acceptor and its reduced form.

2. The improved process of claim 1 wherein the tertiary aldehyde is a compound selected from those of the formula:

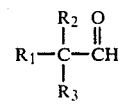

wherein $R_1$, $R_2$ and $R_3$ are each independently selected from the group consisting of alkyl, alkenyl; and $R_1$ and $R_2$ taken together with the carbon atom to which they are attached represent cycloalkyl of 5 to 6 carbon atoms, inclusive, or cycloalkenyl of 5 to 6 carbon atoms, inclusive; the selected compound having a boiling point within the range of from about 75° C. to 200° C.

3. The improved process according to claim 2 wherein the tertiary aldehyde is trimethylacetaldehyde.

4. The improved process according to claim 2 wherein the tertiary aldehyde is 2,3-dimethyl-pent-4-enal.

5. The improved process according to claim 2 wherein the oxidation is carried out with a molar ratio of geraniol/nerol to tertiary aldehyde in the range of 1.0:0.9 to 1.0:2.0.

6. The improved process of claim 2 carried out at a temperature within the range of from about 10° C. to 60° C.

* * * * *